(12) United States Patent
Gleich

(10) Patent No.: US 7,351,194 B2
(45) Date of Patent: Apr. 1, 2008

(54) ARRANGEMENT FOR INFLUENCING MAGNETIC PARTICLES

(75) Inventor: Bernhard Gleich, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 4 days.

(21) Appl. No.: 10/552,803

(22) PCT Filed: Apr. 2, 2004

(86) PCT No.: PCT/IB2004/050388

§ 371 (c)(1),
(2), (4) Date: Oct. 11, 2005

(87) PCT Pub. No.: WO2004/091393

PCT Pub. Date: Oct. 28, 2004

(65) Prior Publication Data

US 2006/0211939 A1 Sep. 21, 2006

(30) Foreign Application Priority Data

Apr. 15, 2003 (EP) .................................. 03101013

(51) Int. Cl.
*A61N 2/00* (2006.01)
(52) U.S. Cl. ......................................... 600/12; 607/105
(58) Field of Classification Search ............ 606/27–31; 607/103, 105; 600/9–15, 409; 219/634
See application file for complete search history.

(56) References Cited

U.S. PATENT DOCUMENTS

| 4,622,952 | A | * | 11/1986 | Gordon ........................ 600/10 |
| 4,662,359 | A | * | 5/1987 | Gordon ........................ 600/10 |
| 5,622,686 | A | * | 4/1997 | Gordon et al. ............. 424/9.32 |
| 5,658,234 | A | * | 8/1997 | Dunlavy ........................ 600/9 |
| 6,149,576 | A | * | 11/2000 | Gray et al. ..................... 600/9 |
| 6,167,313 | A | * | 12/2000 | Gray et al. ................. 607/103 |
| 6,470,220 | B1 | * | 10/2002 | Kraus et al. ................. 607/103 |
| 6,565,887 | B1 | * | 5/2003 | Gray et al. ................. 424/489 |
| 6,575,893 | B2 | * | 6/2003 | Feucht ........................ 600/13 |
| 6,599,234 | B1 | * | 7/2003 | Gray et al. ................... 600/12 |
| 6,635,009 | B2 | * | 10/2003 | Feucht ........................ 600/13 |
| 6,997,863 | B2 | * | 2/2006 | Handy et al. .................. 600/9 |
| 7,074,175 | B2 | * | 7/2006 | Handy et al. .................. 600/9 |
| 2003/0006773 | A1 | * | 1/2003 | Ries ........................... 324/318 |
| 2003/0129763 | A1 | * | 7/2003 | Chamberlain et al. ...... 436/149 |

\* cited by examiner

*Primary Examiner*—Henry M Johnson, III
*Assistant Examiner*—Victoria W Chen

(57) ABSTRACT

An arrangement for influencing magnetic particles in a region of action with the help of an arrangement for generating magnetic fields, by which there is generated a spatially inhomogeneous magnetic field having at least one zone in which the magnetization of the particles is in a state of non-saturation, whereas it is in a state of saturation in the remaining zone. By moving the zone within the region of action, a change in magnetization is produced that can be detected from outside in a first mode of operation and gives information on the spatial distribution of the magnetic particles in the region of action. In a second mode of operation, the movement is repeated so frequently that the region of action heats up.

10 Claims, 3 Drawing Sheets

ARRANGEMENT FOR INFLUENCING MAGNETIC PARTICLES

The invention relates to an arrangement for influencing magnetic particles in a region of action.

Magnetic particles are relatively easy to detect and can therefore be used for examinations and investigations (particularly medical ones). An apparatus and method of this kind for determining the spatial distribution of magnetic particles in an examination zone (i.e. a region of action), and the use therein of suitable magnetic particles, are described in as yet unpublished German patent application DE10151778.5 (applicant's reference PHDE010289). This patent application will be referred to below as D1. To allow the spatial distribution of magnetic particles in an examination zone to be determined, a spatially inhomogeneous magnetic field is generated that has at least one zone in which the magnetization of the particles is in a state of non-saturation. Changing the position of this zone within the examination zone produces a change in magnetization that can be detected from the outside and that gives information on the spatial distribution of the magnetic particles in the examination zone.

Magnetic particles can also be used to heat their surroundings, particularly in medical hyperthermia. A method and a system of this kind for the local heating of regions of an object by variation of the magnetization of magnetic or magnetizable substances is described in as yet unpublished German patent application DE10238853.9 (applicant's reference PHDE020195). This patent application will be referred to below as D2. To heat the target region (i.e. the region of action) locally, an inhomogeneous magnetic field is generated having a pattern in space of its magnetic field strength such that a first sub-zone having a low magnetic field strength (the magnetic particles are not saturated in it) and a second sub-zone having a higher magnetic field strength are generated in the target region. The position in space of the two sub-zones in the target region is then changed for so long at a given frequency that the particles heat up to a desired temperature due to a frequent change in magnetization.

It is therefore an object of the invention to develop an apparatus and a method by which magnetic particles can be influenced in a more varied way.

This object is achieved with an arrangement for influencing magnetic particles in a region of action, which arrangement has:

a) means for generating a magnetic field having a pattern in space of its magnetic field strength such that a first sub-zone (301) having a low magnetic field strength and a second sub-zone (302) having a higher magnetic field strength are formed in the region of action, b) means for changing the position in space of the two sub-zones in the region of action so that the magnetization of the particles changes locally, c) means for acquiring signals, which signals depend on the magnetization in the region of action, which magnetization is influenced by the change in the position in space, d) an analyzing unit for obtaining information, from the signals, on the magnetic particles in the region of action, e) a control unit for controlling the means in such a way that in a first mode of operation, the position of the two sub-zones is changed, the signals resulting therefrom are acquired, and information on the spatial distribution of the magnetic particles in the region of action is determined from the signals, in a second mode of operation, the position in space of the two sub-zones is changed for so long, and at a frequency such, that at least part of the region of action is thereby heated up.

In this arrangement, a spatially inhomogeneous magnetic field having a first sub-zone of low magnetic field strength and a second sub-zone of higher magnetic field strength is generated in a region of action in which magnetic particles are situated. By using appropriate means, the position in space of the two sub-zones can be changed. A more exact description of the generation of the inhomogeneous magnetic field and of the change in the position of the sub-zones is given in detail in D1 or D2. In a first mode of operation of the arrangement according to the invention, the signals from the magnetic particles, which signals are generated by the change in the position in space, are acquired and information on the spatial distribution of the particles is obtained from them. In a second mode of operation, a region for heating-up, which is at least part of the region of action, is heated up by a frequent change in the position in space. It is therefore possible with the arrangement according to the invention for an object both to be examined with regard to the spatial distribution of the magnetic particles situated in it (first mode of operation) and for parts of the object to be heated up (second mode of operation). The various means or components of the arrangement may be used for both modes of operation in this case and no additional components are required to operate the arrangement in the different modes of operation. The different modes of operation are obtained by virtue of the fact that the control unit controls the existing components differently in the respective cases.

In particular, the arrangement allows the magnetic particles to be influenced in one and the same region of action during the different modes of operation without the position in space of the region of action relative to the means or components of the arrangement being changed. In a first step, the spatial distribution of the magnetic particles in an object may, for example, be determined (in the form of an image, for example) in the first mode of operation. A region for heating-up can be determined from this information on distribution. In a second step, the region of the object for heating-up that was defined previously is then heated up in the second mode of operation, in which case this heating-up may take place with high precision in space because the spatial information on the distribution of the magnetic particles that was used in the planning can be used directly for determining the region for heating-up. This is possible because the same components of the arrangement are used in both steps and there is no need for the object to change its position in relation to the components or to the region of action or region for heating-up.

The field of use of the arrangement according to the invention can be extended by performing the first and second modes of operation in a combined form in a third mode of operation. In the third mode of operation, parts of the region of action can be heated up and information on the position in space of the magnetic particles can be obtained at the same time. This is possible because the position in space of the two sub-zones is also changed during the heating-up, as a result of which signals from which information can be obtained on the spatial distribution of the magnetic particles are generated by the magnetic particles (in a similar way to what happens in the first mode of operation).

The gradient field of the arrangement according to the invention may, for example, be generated with permanent magnets. An inhomogeneous magnetic field that has a small, first sub-zone of low field strength surrounded by a second sub-zone of greater field strength forms in the region between two poles of the same polarity. Only in the particles that are situated in the zone around the point at which the field is zero (the first sub-zone) is the magnetization not saturated. In the particles outside this zone the magnetization is in a state of saturation. To make the gradient field switchable or easily adjustable, rather than an arrangement having permanent magnets there is provided a gradient coil arrangement for generating, in the region of action, a gradient field that is similar to the magnetic field described above. If the gradient coil arrangement comprises for example two windings of the same kind which are arranged on the two sides of the target region but through which currents flow in opposite directions (Maxwell coils), then the magnetic field in question is zero at a point along the axis of the windings and increases almost linearly at opposite polarities on the two sides of this point.

One possible way of changing the position in space of the two sub-zones is for a coil and/or permanent-magnet arrangement (or parts thereof) intended for generating the magnetic field on the one hand, or the object containing the magnetic particles on the other hand, to be moved relative to one another. This is a preferred method when very small objects are being examined with very high gradients (microscopy). One embodiment of the present system does not require any mechanical movements. If this magnetic field follows a suitable pattern over time and is suitably oriented, the zero point of the field can pass through the region of action in this way. The position in space of the two sub-zones can be changed relatively quickly in this case, which provides additional advantages for the acquisition of signals that depend on the magnetization in the region of action.

The variation in magnetization that goes hand in hand with the displacement of the zero point of the field can be detected. The coil used for receiving the signals generated in the examination zone may in this case be a coil that is already being used to generate the magnetic field in the examination zone. There are, however, also advantages in using a separate coil for reception, because this coil can be decoupled from the coil arrangement that generates a temporally variable magnetic field and in this way can be optimized in respect of the reception of the signals. Also, an improved signal-to-noise ratio can be obtained with a coil, but even more so with a plurality of coils.

Magnetic particles that are described in D1 and D2 may, for example, be used in the arrangements and methods that have been and will be elucidated. In this regard, the reader is explicitly referred to D1 and D2.

The object is also achieved by a method for influencing magnetic particles in a region of action, which method has the following steps:

a) generation of a magnetic field having a pattern in space of its magnetic field strength such that a first sub-zone (301) having a low magnetic field strength and a second sub-zone (302) having a higher magnetic field strength are formed in the region of action, b) changing the position in space of the two sub-zones in the region of action so that the magnetization of the particles changes locally, c) acquiring signals that depend on the magnetization in the region of action, which magnetization is influenced by the change in the position in space, d) analyzing the signals to obtain information on the spatial distribution of the magnetic particles in the region of action, e) defining a region for heating-up that is at least part of the region of action, f) changing the position in space of the two sub-zones in the region of action for so long, and at a frequency such, that the region for heating-up that has been defined heats up.

For the local heating-up of the magnetic particles, the position in space of the two sub-zones of the magnetic field is changed continuously. In a similar way to what occurs in step b) of the method, this produces signals from which details relating to the spatial distribution of the magnetic particles can be derived. If these signals are acquired, then information on the spatial distribution can be produced at the same time during the heating-up.

These and other aspects of the invention are apparent from and will be elucidated with reference to the embodiments described hereinafter.

Figure 4A:
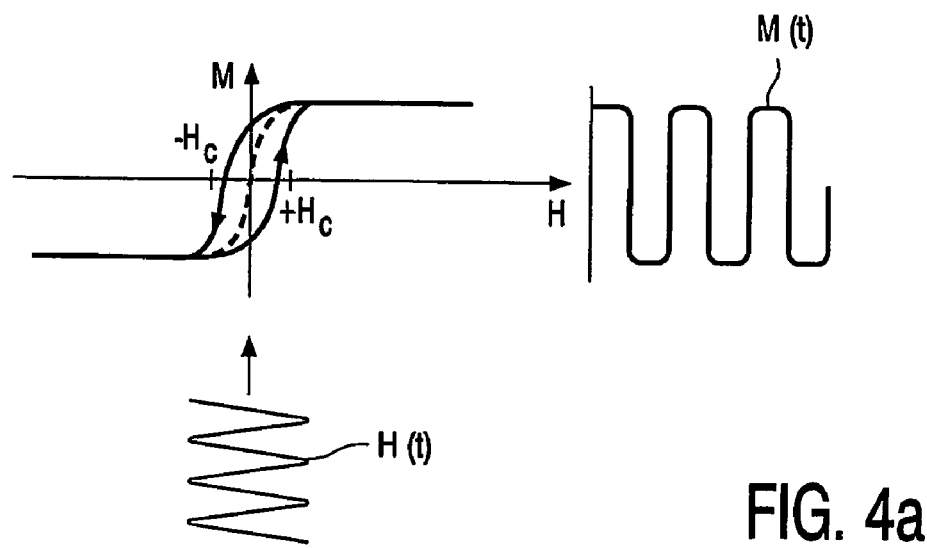
Figure 4B:
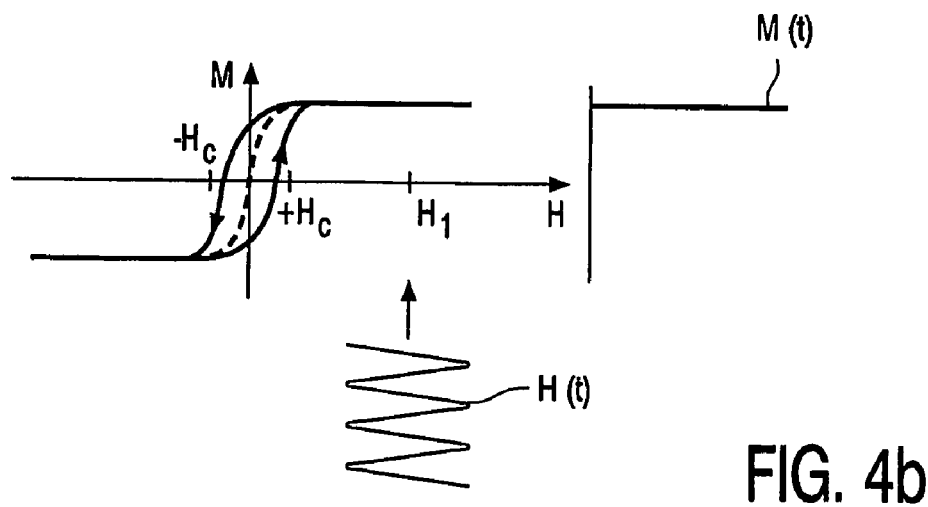

FIGS. 4*a* and 4*b* show the magnetization characteristic of particles of this kind.

Figure 1:
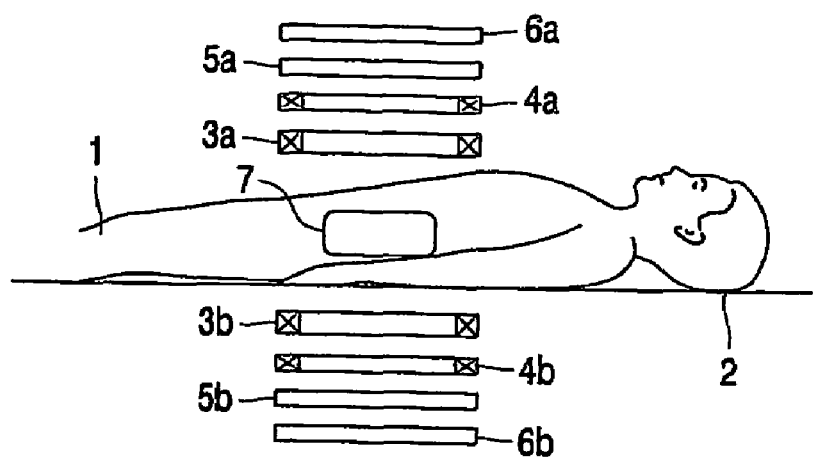
FIG. 1 shows an apparatus for performing the method according to the invention.
Figure 5:
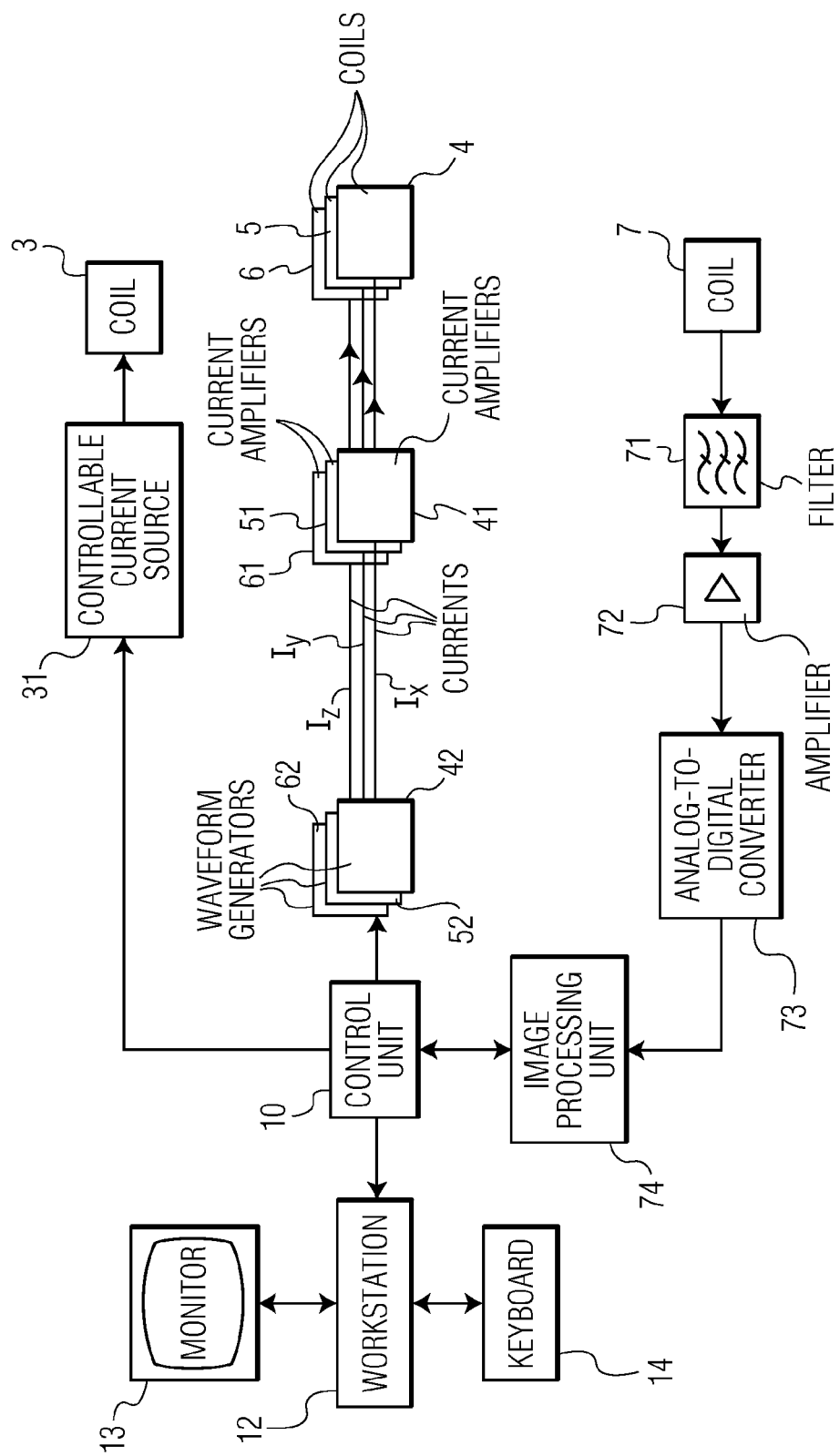

FIG. 5 is a block circuit diagram of the arrangement shown in FIG. 1.

In FIG. 1, reference numeral 1 refers to an object for examination or investigation, a patient in this case, who is situated on a patent presentation table of which only part of the plate 2 is indicated. Before an examination of, for example, the gastro-intestinal tract, a liquid or meal containing magnetic particles is administered to the patient 1.

Figure 3:
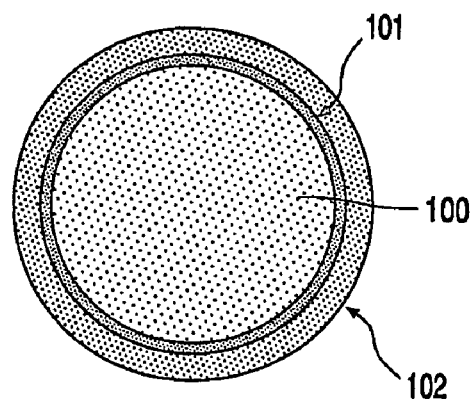
FIG. 3 shows one of the magnetic particles present in the region of action.

A particle of this kind is shown in FIG. 3. It comprises a spherical substrate 100, of glass for example, which is coated with a soft-magnetic layer 101 that is composed of, for example, an iron-nickel alloy (for example, Permalloy). This layer may be covered, for example, by means of a coating layer 102 that protects the particle against acids. The strength of the magnetic field required for the saturation of the magnetization of such particles is dependent on the diameter of the particles. In the case of a diameter of 10 μm, a magnetic field of 1 mT is required for this purpose, whereas in the case of a diameter of 100 μm a magnetic field of 100 mT suffices. Even smaller values are obtained when a coating of a material having a lower saturation magnetization is chosen.

FIGS. 4*a* and 4*b* show the magnetization characteristic, that is, the variation of the magnetization M as a function of the field strength H, in a dispersion containing such particles. It can be seen that the magnetization M no longer changes above a field strength +Hc and below a field strength −Hc, which means that a saturated magnetization exists. The magnetization is not saturated between the values +Hc and −Hc.

FIG. 4*a* illustrates the effect of a sinusoidal magnetic field H(t) if no further magnetic field is active. The magnetization reciprocates between its saturation values at the rhythm of the frequency of the magnetic field H(t). The resultant variation over time of the magnetization is denoted by the reference M(t) in FIG. 4*a*. It can be seen that the magnetization likewise changes cyclically, by which means a similarly cyclic signal is induced outside the coil. As a result of the non-linearity of the magnetization characteristic, this signal is no longer purely sinusoidal in form but contains harmonics, i.e. higher harmonics of the sinusoidal fundamental wave. These harmonics, which can easily be separated off from the fundamental wave, are a measure of the particle concentration.

The dashed part of the line at the center of the curve denotes the approximate mean variation of the magnetization as a function of the field strength. As a deviation from this center line, the magnetization extends slightly to the right when the magnetic field H increases from $-H_c$ to $+H_c$ and slightly to the left when the magnetic field H decreases from $+H_c$ to $-H_c$. This known effect is called a hysteresis effect and underlies a mechanism for the generation of heat. The hysteresis surface area which is formed between the paths of the curve and whose shape and size are dependent on the material, is a measure of the generation of heat upon variation of the magnetization.

FIG. 4b shows the effect of a sinusoidal magnetic field H(t) on which a static magnetic field H1 is superposed. Because the magnetization is in the saturated state, it is practically uninfluenced by the sinusoidal magnetic field H(t). The magnetization M(t) remains constant over time at this area. Consequently, the magnetic field H(t) does not cause a change of the state of the magnetization and does not give rise to a detectable signal that can be detected with a suitable coil.

Figure 2:
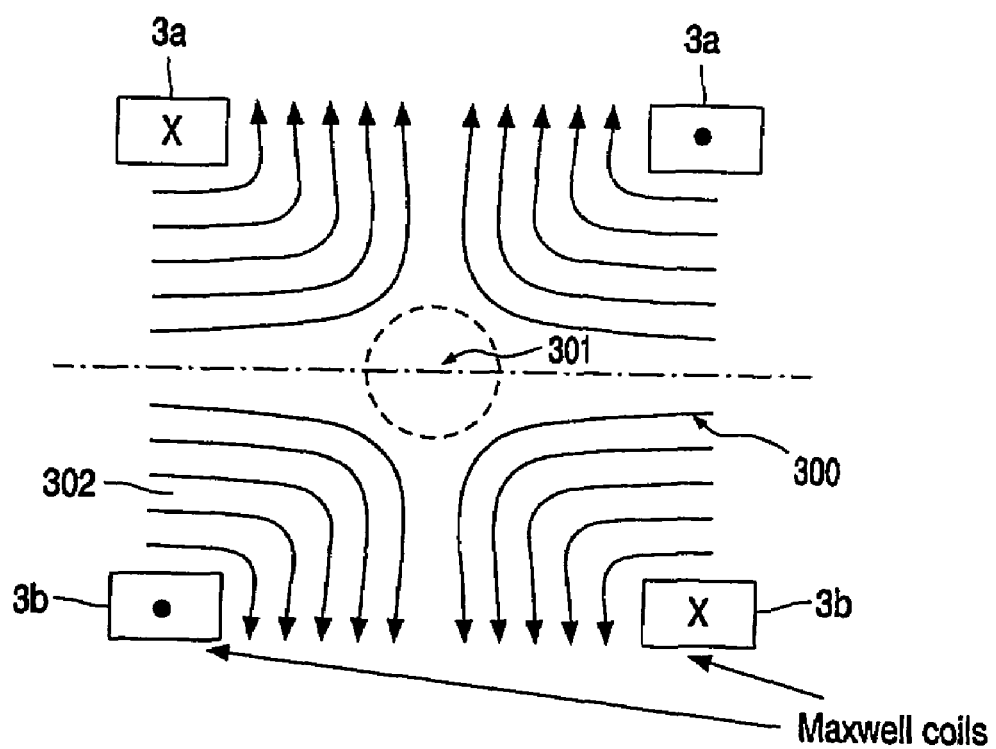
FIG. 2 shows the pattern of field lines generated by the coil arrangement contained in the apparatus.

In the invention, a spatially inhomogeneous magnetic field is generated by appropriate means in a region of action in which magnetic particles are situated. Such means may, for example, be permanent magnets, or electrical conductors as in coils, through which electrical currents flow in the operating state. The magnetic field generated comprises a first sub-zone of low magnetic field strength and a second magnetic sub-zone of higher magnetic field strength. The magnetization of those magnetic particles that are situated in the second sub-zone is in a state of saturation. The magnetization of those magnetic particles that are situated in the first sub-zone is not saturated. To obtain any details of the spatial concentration of the magnetic particles in the object 1 being examined, there are, above and below the patient 1 and the plate of the table, a plurality of pairs of coils, whose region of action defines the examination zone (FIG. 1). A first pair of coils 3 comprises the two windings 3a and 3b of identical construction that are arranged co-axially above and below the patient and through which currents of equal size but opposite directions of circulation flow. The gradient magnetic field generated by them is shown in FIG. 2 by means of the field lines 300. Its gradient in the direction of the (vertical) axis of the pair of coils is almost constant and at one point along this axis it reaches a value of zero. Starting from this field-free point, the strength of the magnetic field increases in all three directions in space with increasing distance from the point. In a zone 301 (the first sub-zone) around the field-free point, which zone is indicated by a dashed line, the field strength is so low that the magnetization of magnetic particles situated in it is not saturated, whereas outside the zone 301 it is in a state of saturation.

The size of the zone 301 determines the spatial resolution of the apparatus and is dependent on the one hand on the magnitude of the gradient of the gradient magnetic field and on the other hand on the strength of the magnetic field required for saturation. For a diameter of 10 μm of the sphere shown in FIG. 3, this strength amounts to 1 mT and to 100 μT for the latter value and a gradient of 0.2 T/m of the magnetic field, the zone 301 in which the magnetization of the particles is not saturated has a dimension of 1 mm.

If a further magnetic field is superimposed on the gradient magnetic field in the region of action, then the zone 301 shifts in the direction of this further magnetic field, the size of the shift increasing with the strength of the magnetic field. If the magnetic field superimposed is temporally variable, then the position of zone 301 changes with time and in space accordingly.

To generate these temporally variable magnetic fields for any desired direction in space, three further pairs of coils are provided. Pair of coils 4, having windings 4a and 4b, generate a magnetic field that extends in the direction of the axis of the coils forming pair of coils 3a, 3b, i.e. vertically. For this purpose, the two windings have currents of equal size flowing through them in the same direction of circulation. In principle, the effect achievable with this pair of coils can also be achieved by superimposing currents in the same direction on the equal but opposite currents in the pair of coils 3a, 3b, as a result of which the current in one pair of coils will decrease and that in the other pair will increase. It may, however, be of advantage if the temporally constant gradient magnetic field and the temporally variable vertical magnetic field are generated by separate pairs of coils.

In order to generate magnetic fields that extend horizontally in space in the longitudinal direction of the patient and in a direction perpendicular thereto, there are provided two further pairs of coils having windings 5a, 5b and 6a, 6b. If pairs of coils of the Helmholz type, like the coil pairs 3a, 3b and 4a, 4b, were used for this purpose, these pairs of coils would have to be arranged to the left and to the right of the examination zone or in front of and behind the examination zone. The accessibility of the region of action would thus be impeded.

Therefore, the windings 5a, 5b and 6a, 6b of the coil pairs are likewise arranged above and below the region of action and their winding configuration must therefore be different from that of the coil pair 4a, 4b. Coils of this kind, however, are known from the field of magnetic resonance apparatus with open magnets (open MRI) in which an RF coil pair is situated above and below the region of action, said RF coil pair being capable of generating a horizontal, temporally variable magnetic field. Therefore, the construction of such coils need not be further elaborated on here.

Finally, there is also shown in FIG. 1 a further coil 7 the purpose of which is to detect signals generated in the region of action. In principle, any of the pairs of field-generating coils 3 to 6 could be used for this purpose. There are, however, advantages in using a separate receiving coil. A better signal-to-noise ratio is obtained (particularly if a plurality of receiving coils are used), and the coil can be so arranged and switched that it is decoupled from the other coils.

FIG. 5 is a block circuit diagram of the apparatus shown in FIG. 1. The diagrammatically indicated pair of coils 3 (the suffixes a and b have been omitted from all the pairs of coils in FIG. 5 for the sake of simplicity) are supplied by a controllable current source 31 with d.c. current that can be controlled—and switched on and off—by a control unit 10. The control unit 10 cooperates with a workstation 12 that is provided with a monitor 13 for showing images representing the distribution of the particles in the region of action. Inputs can be made by a user via a keyboard or some other inputting unit 14.

The pairs of coils 4, 5, 6 receive their currents from current amplifiers 41, 51 and 61. The waveforms over time of the currents Ix, Iy and Iz to be amplified, which currents generate the desired magnetic fields, are preset by respective waveform generators 42, 52 and 62. The waveform generators 42, 52, 62 are controlled by the control unit 10, which calculates the waveform over time required for the particular examination, investigation or treatment procedure and loads it into the waveform generators. In the course of the examination, investigation or treatment, these signals are read out from the waveform generators and fed to the amplifiers 41, 51, 61, which generate the currents required for the pairs of coils 4, 5 and 6 from them.

Generally speaking, a non-linear relationship exists between the shift of the zone 301 from its position at the center of the gradient coil arrangement 3 and the current through the gradient coil arrangement. Moreover, all three coils must generally generate a magnetic field if the zone 301 is to be shifted in position along a straight line extending off the center. Where the waveform of the currents with time is preset, this is allowed for by the control unit, with the help of suitable tables, for example. The zone 301 can therefore be shifted through the region of action along paths of any desired shape.

The signals that are received by the coil 7 in the first mode of operation are fed to an amplifier 72 via a suitable filter 71. The output signals from the amplifier 72 are digitized by an analog-to-digital converter 73 and fed to an image-processing unit 74, which reconstructs the spatial distribution of the particles from the signals and from the position that the zone 301 is occupying at the time during the reception of the signals. The reader is referred at this point to D1 for an exact description of the reconstruction from the signals received by coil 7. From the reconstructed signals, an image is generated that is shown on the monitor 13 of the workstation 12.

With the help of the inputting unit 14 of the workstation 12, the user can mark in the image those regions that are to be heated in the next step. This may, for example, be done by the user specifying such regions interactively by tracing round the regions to be heated with a computer mouse. The workstation 12 determines from this the positions of the regions to be heated and passes on this positional information to the control unit 10. In the second mode of operation, in which the apparatus then operates, the regions selected for heating-up are in fact heated up. In a similar way to the imaging, a displacement of the field-free point in line with the positional information is brought about, with the help of the pairs of coils 4, 5 and 6, by the control unit 10, which controls the waveform generators 42, 52, 62 accordingly.

For particles which contribute to the heating-up due to mechanical motion, a value of, for example, $$130\frac{\text{Hz}\,m}{A}$$

can be used as a guideline value for the frequency of the magnetic field variation (for the particles shown in FIG. 3, for example, frequencies of $$25\frac{\text{kHz}\,m}{A} \text{ or } 250\frac{\text{kHz}\,m}{A}$$

can be used in dependence on the layer properties), so that a frequency of approximately 1 MHz is obtained for a field strength of the magnetic field of $$8\cdot 10^3\frac{A}{m}$$

as required for complete magnetic reversal. This frequency is imposed on one of the three pairs of coils 4, 5 or 6, such as pair of coils 4 for example, so that the region of action is influenced by an alternating field and the magnetic field zone 301 is continuously shifted in a rapidly oscillating fashion in the direction of the magnetic field of the pair of coils 4. As a result, a quasi-one-dimensional zone of a length that can be adjusted by way of the amplitude of the corresponding coil current is heated as a target region in the treatment region (in the case of a spherical shape of the zone 301, an elongate cylindrical region is obtained instead of the strip). The total heating power applied to this strip is thus dependent on, inter alia, the frequency and the amplitude of the alternating field (given by the length in space of the strip), as well as on the field strength required for the maximum development of heat (for example, saturation field strength). The higher the frequency, the higher the heating power will be. The rapidly oscillating magnetic field zone 301 is moved in the other dimensions by means of the other two pairs of coils 5 and 6, so that the entire region for heating-up is heated. The width of the strip may vary at the same time in this case. Reference should be made to document D2 for further details.

In place of the particles having a soft-magnetic coating that were elucidated in connection with FIG. 3, other magnetic particles may also be used. Such particles, together with suitably modified ways of shifting the magnetic field zone 301, are also described in D2.

In a third mode of operation, regions selected for heating-up are heated up exactly as in the second mode of operation. Images of the region of action are shown on the monitor 13 at the same time. This is possible because the zone 301 is shifted even during the heating-up, and as a result, as in the first mode of operation, signals are generated from which images of the region of action can be reconstructed and shown.

The invention claimed is:

1. An arrangement for influencing magnetic particles in a region of action, the arrangement comprising:
   means for generating a magnetic field having a pattern in space of its magnetic field strength such that a first sub-zone having a low magnetic field strength and a second sub-zone having a higher magnetic field strength are formed in the region of action,
   means for changing the position in space of the two sub-zones in the region of action so that the magnetization of the particles changes locally,
   means for acquiring signals, which signals depend on the magnetization in the region of action, which magnetization is influenced by the change in the position in space,
   an analyzing unit for obtaining information, from the signals, on the magnetic particles in the region of action,
   a control unit for controlling the means in such a way that in a first mode of operation, the position of the two sub-zones is changed, the signals resulting therefrom are acquired, and information on the spatial distribution of the magnetic particles in the region of action is determined from the signals, in a second mode of operation, the position in space of the two sub-zones is changed for so long, and at a frequency such, that at least part of the region of action is thereby heated up, wherein the means for generating the magnetic field comprise a gradient coil arrangement for generating a gradient magnetic field that reverses its direction and has a zero crossing in the first sub-zone.

2. The arrangement as claimed in claim 1, wherein the control unit controls the means to execute the second mode of operation simultaneously acquire the signals resulting from the change in the position of the two sub-zones and determine information on the spatial distribution of the magnetic particles in the region of action.

3. An arrangement as claimed in claim 1, wherein the signals induced in the region of action by a temporal variation in the magnetization are received by a coil arrangement.

4. An arrangement for influencing magnetic particles in a region of action comprising:
   means for generating a magnetic field having a pattern in space of its magnetic field strength such that a first sub-zone having a low magnetic field strength and a second sub-zone having a higher magnetic field strength are formed in the region of action,
   means for changing the position in space of the two sub-zones in the region of action so that the magnetization of the particles changes locally,
   means for acquiring signals, which signals depend on the magnetization in the region of action, which magnetization is influenced by the change in the position in space,
   an analyzing unit for obtaining information, from the signals, on the magnetic particles in the region of action,
   a control unit for controlling the means in such a way that
   in a first mode of operation, the position of the two sub-zones is changed, the signals resulting therefrom are acquired, and information on the spatial distribution of the magnetic particles in the region of action is determined from the signals,
   in a second mode of operation, the position in space of the two sub-zones is changed for so long, and at a frequency such, that at least part of the region of action is thereby heated up, wherein the two sub-zones in the region of action are shifted in position by a temporally variable magnetic field that is superimposed on a gradient magnetic field.

5. A method for influencing magnetic particles in a region of action comprising the acts of:
   generation of a magnetic field having a pattern in space of its magnetic field strength such that a first sub-zone having a low magnetic field strength and a second sub-zone having a higher magnetic field strength are formed in the region of action,
   changing the position in space of the two sub-zones in the region of action so that the magnetization of the particles changes locally,
   acquiring signals that depend on the magnetization in the region of action, wherein magnetization is influenced by the above change in position,
   analyzing the signals to obtain information on the spatial distribution of the magnetic particles in the region of action,
   defining a region for heating-up that is at least part of the region of action,
   changing the position in space of the two sub-zones in the region of action for a time and at a frequency so that the defined region heats up,
   shifting the position of the two sub-zones in the region of action by a temporally variable magnetic field that is superimposed on a gradient magnetic field.

6. The method as claimed in claim 5, wherein the steps of acquiring signals that depend on the magnetization in the region of action, wherein the magnetization is influenced by the above change in position, and
   analyzing the signals to obtain information on the spatial distribution of the magnetic particles in the region of action
   are also performed during the heating-up of the defined region.

7. A system for influencing magnetic particles in a region of action comprising:
   a generator configured to generate a magnetic field comprising a pattern in space of its magnetic field strength such that a first sub-zone having a low magnetic field strength and a second sub-zone having a higher magnetic field strength are formed in the region of action,
   a position changer configured to change the position in space of the two sub-zones in the region of action so that the magnetization of the particles changes locally,
   an signal acquirer configured to acquire signals, which signals depend on the magnetization in the region of action, which magnetization is influenced by the change in the position in space,
   an analyzing unit configured to obtain information, from the signals, on the magnetic particles in the region of action,
   a control unit configured to control a first mode of operation wherein the position of the two sub-zones is changed, the signals resulting are acquired, and information on the spatial distribution of the magnetic particles in the region of action is determined from the signals, and configured to control a second mode of operation wherein the position in space of the two sub-zones is changed at a frequency such that at least part of the region of action is thereby heated up,
   wherein the magnetic field generator comprises a gradient coil arrangement configured to generate a gradient magnetic field that reverses its direction and has a zero crossing in the first sub-zone.

8. A system for influencing magnetic particles in a region of action comprising:
   a generator configured to generate a magnetic field comprising a pattern in space of its magnetic field strength such that a first sub-zone having a low magnetic field strength and a second sub-zone having a higher magnetic field strength are formed in the region of action,
   a position changer configured to change the position in space of the two sub-zones in the region of action so that the magnetization of the particles changes locally,
   an signal acquirer configured to acquire signals, which signals depend on the magnetization in the region of action, which magnetization is influenced by the change in the position in space,
   an analyzing unit configured to obtain information, from the signals, on the magnetic particles in the region of action,
   a control unit configured to control a first mode of operation wherein the position of the two sub-zones is changed, the signals resulting are acquired, and information on the spatial distribution of the magnetic particles in the region of action is determined from the signals, and configured to control a second mode of operation wherein the position in space of the two sub-zones is changed at a frequency such that at least part of the region of action is thereby heated up, wherein the two sub-zones in the region of action are shifted in position by a temporally variable magnetic field that is superimposed on a gradient magnetic field.

9. The arrangement in claim 7, wherein the control unit is configured to execute the second mode of operation, to acquire the signals resulting from the change in the position of the two sub-zones and to determine information on the spatial distribution of the magnetic particles in the region of action simultaneously.

10. The arrangement in claim 8, wherein the signals induced in the region of action by a temporal variation in the magnetization are received by a coil arrangement.

* * * * *